United States Patent [19]

Buehler et al.

[11] Patent Number: 4,605,551

[45] Date of Patent: Aug. 12, 1986

[54] DRY OIL COATED ANTACID PROCESS

[75] Inventors: John D. Buehler, Germantown, Tenn.; Hans J. Medal, Fort Washington; Gregory A. Rhoa, Collegeville, both of Pa.

[73] Assignee: William H. Rorer, Inc., Fort Washington, Pa.

[21] Appl. No.: 676,634

[22] Filed: Nov. 30, 1984

[51] Int. Cl.$^4$ ............... A61K 9/42; A61K 33/06; A61K 33/08; A61K 33/10
[52] U.S. Cl. ............... 424/38; 424/154; 424/155; 424/156; 424/157
[58] Field of Search ............... 424/38, 154, 155, 156, 424/157

[56] References Cited

U.S. PATENT DOCUMENTS

| | | | |
|---|---|---|---|
| 3,843,778 | 10/1974 | Diamond et al. | 424/38 |
| 4,327,076 | 4/1982 | Puglia et al. | 424/38 |
| 4,327,077 | 4/1982 | Puglia et al. | 424/38 |
| 4,533,543 | 8/1985 | Morris et al. | 424/38 |

Primary Examiner—Shep K. Rose
Attorney, Agent, or Firm—James A. Nicholson; Alexis Barron; Martin F. Savitzky

[57] ABSTRACT

This invention relates to an improvement comprising coating agitated particles of substantially anhydrous antacid with a solvent-free mixture of electronegatively charged material in a non-toxic inert substantially water insoluble oil.

8 Claims, No Drawings

DRY OIL COATED ANTACID PROCESS

FIELD OF THE INVENTION

The present invention relates to antacids useful in the treatment of gastrointestinal hyperacidity, and, particularly, to processes for the preparation of antacid compositions.

One of the mainstays of the treatment of gastrointestinal hyperacidity and ulcers is the utilization of orally administerable antacid compositions. The most common forms for the administration of these compositions are suspensions and chewable tablets. The preferred characteristics of these compositions include: the ability to raise the pH of the stomach to values in the range of about 3 to about 4.5; the nonabsorbability of the composition in the gastrointestinal tract; the absence of undesirable side effects such as diarrhea and constipation; the convenience of dosage form; and, palatability. Many antacid preparations have associated therewith an unpleasant and unpalatable mouth-feel due to the chalkiness, grittiness, dryness and astringent properties of many of the metallic carbonates and hydroxides which are used as antacid ingredients.

There are many techniques available in the pharmaceutical arts for approaching the above-said palatability problem, including the careful selection of flavoring agents, the provision of a coated tablet and the production of compositions comprising oil-coated, antacid particles, the last mentioned being the subject of the present invention.

REPORTED DEVELOPMENTS

U.S. Pat. No. 3,843,778 to Diamond, Joslin and Buehler (assigned to the same assignee as the present application) discloses methods for the preparation of oil-coated antacid particles and suspensions and chewable tablets comprised of said particles. In particular, this patent discloses two methods for the preparation of oil-coated antacid particles. One method comprises the spray coating of dry, antacid particles with a solution of an oil in a nonaqueous solvent. The other method comprises the mixing of an electronegatively charged oil with antacid particles in an aqueous gel system. Both methods require the dispersal of the oil and antacid in a system which includes a volatile liquid carrier and the use of a subsequent step to volatilize the liquid carrier. This subsequent step necessitates normally the removal of the liquid carrier-containing mixture from the mixing apparatus followed by the addition of heat to volatilize the liquid carrier. Only then can additional excipients be added to the antacid preparation. Moreover, these methods require drying equipment and processing times which are not justified economically on a small scale basis. The present invention relates to an oil-coated antacid particle process which is dry and free of a volatile liquid carrier, which no longer requires a liquid carrier removal step subsequent to the coating of the antacid particles, and, which is economical to use on a small, as well as a large, scale.

SUMMARY OF THE INVENTION

The present invention relates to a process and antacid composition produced by said process for the preparation of oil-coated antacid particles wherein particles of an antacid are contacted with a mixture of electronegatively charged material in a non-toxic, inert, substantially water insoluble oil, wherein the improvement comprises coating agitated particles of substantially anhydrous antacid with a solvent-free mixture of electronegatively charged material in said oil.

Another aspect of this invention relates to a process comprising:

(A) providing an electropositively charged antacid in the form of a substantially anhydrous powder;

(B) providing a mixture of an electronegatively charged material in a water insoluble, non-toxic hydrocarbon oil;

(C) rapidly agitating said antacid; and (D) spraying said oil mixture into said rapidly agitated antacid until substantially all of said antacid is coated with said oil.

DETAILED DESCRIPTION OF THE INVENTION

The term "solvent-free" is used in connection with the description of the antacid and oil mixture and means the absence of a liquid carrier which is removed during the process of the present invention.

The antacids useful in the process of this invention are preferably electropositively charged, meaning that its primary and secondary particles have a positive surface charge, and may be one or more compounds recognized in the pharmaceutical art as an antacid. Examples of antacids which may be used in the practice of this invention include aluminum hydroxide, aluminum hydroxycarbonate, aluminum magenesium glycinate, calcium carbonate, dihydroxy aluminum aminoacetate, magnesium aluminate, magnesium carbonate, magnesium hydroxide, magnesium oxide and magnesium trisilicate. A mixture of two or more antacids can be used. Preferred antacids include aluminum hydroxide, calcium carbonate, magnesium carbonate, magnesium hydroxide and magnesium trisilicate. The more preferred antacids include aluminum hydroxide, calcium carbonate and magnesium hydroxide.

The antacid is used in small particle size form, for example, a particle size within the range of about 0.05 to about 300 microns. The preferred particle size is about 1 to about 50 microns, with the most preferred size of particle being about 3 to about 10 microns, as measured by a Coulter Counter.

The oil for use in this invention can be any oil which is substantially water insoluble, inert, and nontoxic. A mixture of two or more oils can be used. Typically, it is a hydrocarbon oil and may be, for example, of vegetable or mineral origin. The oil may be selected from the group including almond oil, coconut oil, corn oil, cottonseed oil, refined linseed oil, light liquid petrolatum, heavy liquid petrolatum, olein, olive oil, palm oil, peanut oil, persic oil, sesame oil, soybean oil, or safflower oil. Preferred oils include corn oil, light and heavy liquid petrolatum, olein, olive oil, peanut oil and soybean oil. The more preferred oils are corn oil and light and heavy liquid petrolatum.

The electronegatively charged material in admixture with said oil is a material which has a negative surface charge. The electronegatively charged material may be soluble or insoluble in the oil phase of the mixture and is preferably insoluble and dispersed in the oil phase in the form of a colloidal suspension or slurry. A mixture of two or more electronegatively charged materials may be used. Examples of such materials include: a surfactant such as an alkyl aryl sulfonate, an alkyl sulfate, a sulfonated amide or amine, a sulfated or sulfonated ester or ether, an alkyl sulfonate, and a dioctyl sulfosuccinate and the like; a hydrated aluminum silicate such as micronized bentonite or kaolin, a silica pigment, for example, that sold under the trademark of Cab-O-Sil by Cabot Corporation of Boston, Mass., a microfine silica sold under the trademark Quso by Philadelphia Quartz Co. of Philadelphia, Pa., and as FK500LS by Degussa, A. G.

The amount of electronegatively charged material present in the oil phase is such that it is sufficient to charge the oil and thereby form an electronegatively charged oil mixture which is capable of dispersing intimately throughout a substantially anhydrous electropositively charged antacid material. The weight ratio of electronegative material to oil is about 1:100 to about 1:10 and preferably about 3:100 to about 5:100. The oil mixture is formed by slowly adding the electronegative material to the oil and stirring until uniform.

A preferred embodiment of the process of this invention comprises an oil slurry of about 3 to about 4% w/w of microfine silica in mineral oil (otherwise referred to as "light liquid petrolatum").

The electropositive antacid and electronegatively charged oil are brought into contact in a mixing apparatus in which the antacid particles are uniformly coated with said oil, that is, substantially all of the antacid particles. The process of this invention provides for the agitation of the oil and antacid mixture in a manner which inhibits or deters the formation of agglomerates and/or which breaks up agglomerates which may form. Any mixing apparatus which is capable of uniformly dispersing the oil mixture throughout the agitated antacid and which prevents and/or disrupts the formation of agglomerates could be utilized in the process of this invention. A preferred mixing apparatus comprises a mixing chamber which includes a set of rotating devices ("choppers") which rotate at a rate greater than about 2000 rpm and most preferably at a rate greater than about 3000 rpm. A most preferred mixing apparatus also includes in said chamber slower moving mixing devices ("plows") which rotate at a slower rate, for example, about 100 to about 200 rpm.

The antacid particles are rapidly agitated while the oil mixture is dispersed therein to effect the coating of the particles. The introduction of the mixture may be effected by any means available in the art for accomplishing this, for example, by stepwise addition of the oil mixture in predetermined amounts or by feeding a stream of oil mixture through an opening of predetermined size in the mixing apparatus. The preferred means comprises spraying the oil mixture. The oil spray is preferably a uniform and substantially turbulent-free spray having a pressure sufficient to admix the said ingredients in the shortest and most efficient period of time, for example, about two to about four minutes for about 400 kg batch size.

The oil mixture is introduced into the agitated antacid material until the antacid particles are uniformly coated. The ratio of oil to antacid varies depending on a number of factors including the nature of the oil, the particle size and chemistry of the antacid, the mixing device and the particular electronegative material used. The ratio of oil to antacid material is preferably about 1:5 to about 1:2 and most preferably about 1:5 to about 2:5. Other ratios can be used, for example, about 1:10 to about 1:1.

The oil-coated antacid particles prepared according to the present invention may be combined with additional pharmaceutically acceptable materials and formulated into any pharmaceutically acceptable form including tablets, capsules, lozenges, troches, powders, aqueous suspensions, elixirs, syrups, which may contain one or more agents selected from the group including sweetening agents, flavoring agents, coloring agents, and preserving agents. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulfate and talc, can be used in producing tablets. For a capsule form, lactose and high molecular weight polyethylene glycols are among the preferred pharmaceutically acceptable carriers. Where aqueous suspensions for oral use are formulated, the carrier can include an emulsifying or suspending agent. Diluents such as water, ethanol, propylene glycol, and glycerin and their combinations can be employed as well as other pharmaceutically acceptable materials.

A further aspect of the present invention relates to advantages which flow from the production of chewable antacid tablets. The present invention provides means for the formulation of a tablet, including an oil-coated antacid, starting from a mixture of ingredients which is substantially anhydrous and which does not require the additional step of liquid carrier removal prior to further treatment. The substantially anhydrous oil-coated antacid may be mixed with additional excipients and then treated with an aqueous granulating solution to form a wetted granulate comprising a mixture containing large agglomerates of hydrated and excipient laden oil-coated particles which are capable of being dried, milled and compressed into tablets.

A preferred process for the preparation of an antacid tablet comprises:

(A) agitating about 3 to about 10 micron size particles of anhydrous aluminum hydroxide;

(B) spraying a slurry of microfine silica in mineral oil into said agitated aluminum hydroxide until the ratio of said mineral oil to said aluminum hydroxide is about 1:5 to about 2:5;

(C) continuing said agitation during said spraying at a rate effective to eliminate the formation of agglomerates and until substantially all of said aluminum hydroxide particles are substantially coated with oil thereby forming an oil-coated antacid;

(D) dispersing uniformly a mixture of magnesium hydroxide powder and tablet forming excipients throughout said oil-coated antacid, thereby forming a pregranulate mixture;

(E) adding to said pre-granulate mixture, an aqueous granulating solution and continuing said agitation until said pregranulate mixture achieves an effective degree of wetness, thereby forming a wetted granulate;

(F) drying, milling and compressing said wetted granulate into tablets.

A preferred embodiment of the tablet-forming process utilizes a slurry of microfine silica in mineral oil (about 3 to about 4% w/w), tablet-forming excipients including mannitol powder and microcrystalline cellulose, and a granulating aqueous solution of sodium saccharin, sorbitol and citric acid. Additional excipients such as lubricants and flavors also may be added to the dried granulate prior to compression into tablets.

The following preparations are examples of the practice of the present invention.

EXAMPLE 1

| | Amount |
|---|---|
| aluminum hydroxide dry gel | 11.0 kg |
| light liquid petrolatum | 2.1 kg |
| microfine silica (Quso ™) | 0.1 kg |

Microfine silica is added to the light liquid petrolatum and the constituents are mixed until a uniform slurry is obtained. The slurry is added to the aluminum hydroxide dry gel with stirring and stirring is continued until the mixture is uniform.

When the aluminum hydroxide dry gel in Example 1 is replaced by one or more of the antacids of Table I below, then the corresponding antacid coated with light liquid petrolatum is prepared.

TABLE I
aluminum hydroxycarbonate
aluminum magnesium glycinate
calcium carbonate
dihydroxy aluminum aminoacetate
magnesium aluminate
magnesium carbonate
magnesium hydroxide
magnesium oxide
magnesium trisilicate When the light liquid petrolatum in the above example is replaced by an oil of Table II below, then aluminum hydroxide coated with the corresponding oil is prepared.

TABLE II
almond oil
coconut oil
corn oil
cottonseed oil
refined linseed oil
heavy liquid petrolatum
olein oil
olive oil
palm oil
peanut oil
persic oil
sesame oil
safflower oil When aluminum hydroxide dry gel in the above example is replaced by one or more of the antacids of Table I above and the light liquid petrolatum in the above example is replaced by one of the oils of Table II above, then the corresponding antacid coated with the corresponding oil is prepared.

When the amount of oil in the above example is varied between 0.1 and 2 percent with respect to the weight of the antacid present, then the corresponding coating is obtained.

EXAMPLE 2

The oil-coated aluminum hydroxide of Example 1 is dispersed in an aqueous vehicle with the addition of the adjuncts identified below to provide a stable, palatable suspension of the final composition.

| | Amount (wt percent) |
|---|---|
| coated aluminum hydroxide | 5.0% |
| sorbitol (70% w/w in water) | 2.0% |
| peppermint oil | 0.004% |
| saccharin | 0.0225% |
| methyl p-hydroxybenzoate | 0.1% |
| propyl p-hydroxybenzoate | 0.05% |
| distilled water | q.s. |

When the oil-coated aluminum hydroxide of the above example is replaced by one or more of the oil-coated antacids of Table I, then the corresponding suspension is prepared.

EXAMPLE 3

The coated aluminum hydroxide gel of Example 1 is granulated with a 10 percent aqueous starch paste, and the other ingredients identified below are blended in the resulting wetted granulate, which is dried, milled, and compressed into chewable tablets.

| | Amount (wt percent) |
|---|---|
| coated aluminum hydroxide | 50% |
| mannitol granules | 30% |
| sorbitol powder | 18% |
| peppermint oil | 0.01% |
| magnesium stearate | 1.75% |
| saccharin | 0.024% |

When coated aluminum hydroxide of the above example is replaced by one or more of the antacids of Table I, then the corresponding chewable tablet is prepared.

EXAMPLE 4

The following ingredients are used in the amounts indicated to prepare chewable tablets.

| | | | |
|---|---|---|---|
| (A) | dried aluminum hydroxide gel | | 7.5 kg |
| (B) | oil slurry: | (1) mineral oil | 1.63 kg |
| | | (2) microfine silica (Quso ™) | 0.06 kg |
| (C) | magnesium hydroxide | | 6.6 kg |
| | calcium carbonate | | 8.25 kg |
| | mannitol | | 12.4 kg |
| | microcrystalline cellulose (Avicel PH 101) | | 1.9 kg |
| (D) | sodium saccharin | | 0.05 kg |
| | citric acid | | 0.08 kg |
| | sorbitol (70% w/w in water) | | 2.83 kg |
| | water | | 13.2 liter |

The dried aluminum hydroxide gel is introduced into a Littleford-Lodige mixer and the mixer activated (choppers set at about 3500 rpm and plows set at about 125 rpm.) The oil slurry is sprayed into the mixing chamber and the mixer turned off when the entire amount, indicated above, has been added. The mixture of (C) above is added to the mixing chamber and the resulting mixture agitated until uniform. The granulating solution (D) above is added to the mixture during agitation and mixing stopped when the desired degree of wetness is achieved. The resulting granulate is dried on trays at about 150° F. for about 16 to about 24 hours and milled. Flavors are blended with the dried granulate in a blender and the resulting powder is compressed into tablets. The resulting tablets are chewable and palatable and have an excellent ANC (acid neutralizing capacity) value.

We claim:

1. In a process for the preparation of oil-coated antacid particles wherein particles of an antacid are contacted with a mixture of electronegatively charged material in a non-toxic, inert, substantially water insoluble oil, the improvement comprising coating agitating particles of substantially anhydrous antacid with a solvent-free mixture of electronegatively charged material in said oil.

2. A process for the preparation of oil-coated antacid particles comprising:
   (A) providing an electropositively charged antacid in the form of a substantially anhydrous powder;
   (B) providing a mixture of an electronegatively charged material in a water insoluble, non-toxic hydrocarbon oil;
   (C) rapidly agitating said antacid; and
   (D) spraying said oil mixture into said rapidly agitated antacid until substantially all of said antacid is coated with said oil.

3. A process according to claim 2 comprising:
   (A) providing a substantially anhydrous antacid selected from the group including aluminum hydroxide, aluminum hydroxycarbonate, aluminum magnesium glyconate, dihydroxy aluminum aminoacetate, magnesium aluminate, magnesium carbonate, magnesium hydroxide, magnesium oxide, magnesium trisilicate, and calcium carbonate;
   (B) providing a mixture of electronegatively charged material in a water insoluble hydrocarbon oil in an amount sufficient to charge said hydrocarbon oil, wherein said electronegatively charged material is selected from the group consisting of an alkyl aryl sulfate, an alkyl sulfate or sulfonate, a sulfonated amide or amine, a sulfated or sulfonated ester or ether, a dialkyl sulfosuccinate, hydrated aluminum silicate, pigmented silica, and microfine silica;
   (C) agitating said antacid;
   (D) spraying said mixture into said agitated antacid until the proportion of oil to antacid material is between about 1:5 to about 1:2;
   (E) continuing said agitation until said antacid is uniformly coated with said oil mixture.

4. A process according to claim 3, wherein said proportion of oil to antacid is about 1:5 to about 2:5.

5. A process according to claim 4, wherein said antacid is comprised of particles of from about 3 to about 10 microns in size.

6. A process according to claim 5, wherein said oil mixture comprises a slurry of microfine silica in mineral oil.

7. A process according to claim 6, wherein said oil slurry comprises abut 3 to about 4% w/w of microfine silica in mineral oil.

8. A process for the preparation of an antacid tablet comprising:
   (A) agitating about 3 to about 10 microns size particles of substantially anhydrous aluminum hydroxide;
   (B) spraying a slurry of microfine silica in mineral oil into said agitated aluminum hydroxide until the ratio of said mineral oil to said aluminum hydroxide is about 1:5 to about 2:5;
   (C) continuing said agitation during said spraying at a rate effective to eliminate the formation of agglomerates and until substantially all of said aluminum hydroxide particles are substantially coated with oil thereby forming an oil-coated antacid;
   (D) dispersing uniformly a mixture of magnesium hydroxide powder and tablet forming excipients throughout said oil-coated antacid, thereby forming a pre-granulate mixture;
   (E) adding to said pre-granulate mixture, an aqueous granulating solution and continuing said agitation until said pre-granulate mixture achieves an effective degree of wetness, thereby forming a wetted granulate;
   (F) drying, milling and compressing said granulate into tablets.

* * * * *